United States Patent [19]

Igarashi

[11] 4,166,114
[45] Aug. 28, 1979

[54] AMINOGLYCOSIDE ANTIBIOTIC DERIVATIVES AND METHOD OF USE

[75] Inventor: Kikuo Igarashi, Itami, Japan

[73] Assignee: Shionogi & Co., Ltd., Osaka, Japan

[21] Appl. No.: 837,909

[22] Filed: Sep. 29, 1977

[30] Foreign Application Priority Data

Oct. 28, 1976 [JP] Japan .................... 51/130119

[51] Int. Cl.$^2$ .................... A61K 31/71; C07H 15/22
[52] U.S. Cl. .................... 424/180; 260/326.2; 260/326.47; 536/10; 536/17 R; 546/221; 546/242
[58] Field of Search .................... 536/10, 17; 424/180

[56] References Cited

U.S. PATENT DOCUMENTS

| | | | |
|---|---|---|---|
| 3,920,628 | 11/1975 | Daniels | 536/10 |
| 3,929,762 | 12/1975 | Umezawa et al. | 536/10 |
| 3,965,089 | 6/1976 | Umezawa et al. | 536/10 |

Primary Examiner—Johnnie R. Brown
Attorney, Agent, or Firm—Wenderoth, Lind & Ponack

[57] ABSTRACT

Novel aminoglycoside antibiotic derivatives and their salts containing a 2-deoxystreptamine moiety of which the 1-amino group is substituted by a group represented by the formula:

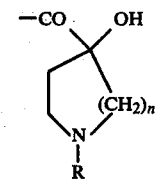

[wherein R is hydrogen atom, lower alkyl or aralkyl; n is an integer 1 or 2]

are effective in treatment and prevention of infectious diseases caused by gram positive and negative bacteria.

19 Claims, No Drawings

AMINOGLYCOSIDE ANTIBIOTIC DERIVATIVES AND METHOD OF USE

I. SUMMARY OF INVENTION

This invention relates to novel aminoglycoside antibiotic derivatives having an excellent antimicrobial action. More particularly, it relates to novel aminoglycoside antibiotic derivatives and their salts containing a 2-deoxystreptamine moiety of which the 1-amino group is substituted by a pyrrolidinecarboxylic acid or piperidinecarboxylic acid.

It has been attempted to improve the antimicrobial activity and its spectrum of aminoglycoside antibiotics by introducing specified acyl group at the 1-amino group of the 2-deoxystreptamine moiety. For instance, amikacin derived from kanamycin A is a representative derivative of which the 1-amino is acylated with 4-amino-2-hydroxybutyric acid. Amikacin is known to be effective against kanamycin resistant bacteria but with approximately the same degree of the toxicity as kanamycin [Kawaguchi et al., J. Antibiotic, 25, 695(1972); U.S. Pat. No. 3,781,268 (1973); Fujisawa et al., J. Antibiotic, 27, 677(1974)].

It has been discovered by the present inventor that the blocking of the 1-amino of aminoglycoside antibiotics with pyrrolidine- or piperidine-carboxylic acid or their N-alkyl derivatives greatly enhances the antimicrobial activity and further draws the activity effective against aminoglycoside resistant strains. The present invention is based upon this finding.

The novel aminoglycoside antibiotic derivatives in this invention can be represented by the following general formula (I):

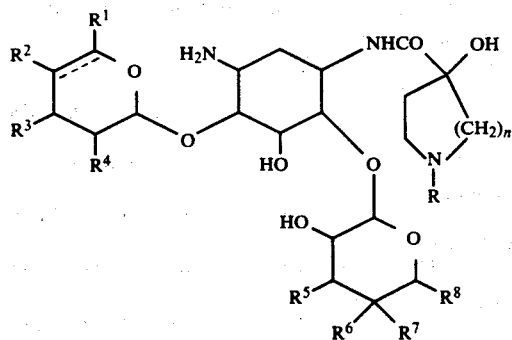

(wherein R is hydrogen atom, lower alkyl or aralkyl; $R^1$ is aminomethyl, hydroxymethyl, methylaminomethyl or 1-methylaminoethyl; $R^2$, $R^3$ and $R^6$ represents independently hydrogen atom or hydroxy; $R^4$ is hydroxy or amino; $R^5$ is amino or methylamino; $R^7$ is hydroxy; or methyl; $R^8$ is hydrogen atom, hydroxy, hydroxymethyl or carbamoyloxymethyl; the dotted line represents the presence or absence of a double bond; n is an integer 1 or 2).

The aminoglycosides used as starting material in this invention containing 2-deoxystreptamine moiety are represented by the general formula (II):

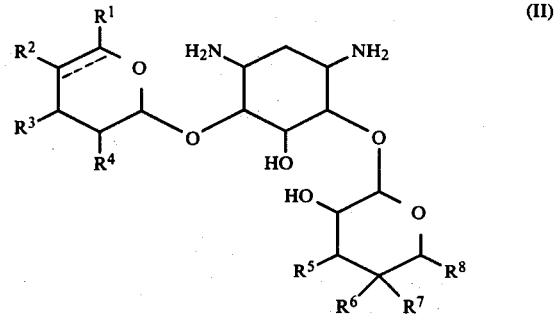

(wherein $R^1$-$R^8$ and the dotted line have the same meaning as mentioned above). Representative of the compounds (II) include tobramycin ($R^1$=CH$_2$NH$_2$; $R^2$=OH; $R^3$H; $R^4$=NH$_2$; $R^5$=NH$_2$; $R^6$=H; $R^7$=OH; $R^8$=CH$_2$OH)[produced by Streptomyces tenebrarius ATCC 17920 and 17921; U.S. Pat. No. 3,691,279], kanamycin A ($R^1$=CH$_2$NH$_2$; $R^2$=OH; $R^3$=OH; $R^4$=OH; $R^5$=NH$_2$; $R^6$=H; $R^7$=OH; $R^8$=CH$_2$OH), kanamycin B ($R^1$=CH$_2$NH$_2$; $R^2$=OH; $R^3$=OH; $R^4$=NH$_2$; $R^5$=NH$_2$; $R^6$=H; $R^7$=OH; $R^8$=CH$_2$OH), and kanamycin C ($R^1$=CH$_2$OH; $R^2$=OH; $R^3$=OH: $R^4$=NH$_2$; $R^5$=NH$_2$; $R^6$=H; $R^7$=OH; $R^8$=CH$_2$OH)[produced by Streptomyces kanamyceticus ATCC 12853 and 21252; U.S. Pat. No. 2,931,798], dideoxykanamycin B (dibekacin) ($R^1$=CH$_2$NH$_2$; $R^2$=H; $R^3$=H; $R^4$=NH$_2$; $R^5$=NH$_2$; $R^6$=H; $R^7$=OH; $R^8$=CH$_2$OH)[produced by Streptomyces kanamyceticus ATCC 21259, 21260 and 21261; U.S. Pat. No. 3,753,973], gentamicin C$_1$ ($R^1$=CH(CH$_3$)NHCH$_3$; $R^2$=H; $R^3$=H; $R^4$=NH$_2$; $R^5$=NHCH$_3$; $R^6$=OH; $R^7$=CH$_3$; $R^8$=H), gentamicin C$_2$ ($R^1$=CH(CH$_3$)NH$_2$; $R^2$=H; $R^3$=H; $R^4$=NH$_2$; $R^5$=NHCH$_3$; $R^6$=OH; $R^7$=CH$_3$; $R^8$=H), gentamicin C$_{1a}$ ($R^1$=CH$_2$NH$_2$; $R^2$=H; $R^3$=H; $R^4$=NH$_2$; $R^5$=NHCH$_3$; $R^6$=OH; $R^7$=CH$_3$; $R^8$=H) and gentamicin B ($R^1$=CH$_2$NH$_2$; $R^2$=OH; $R^3$=OH; $R^4$=OH; $R^5$=NHCH$_3$; $R^6$=OH; $R^7$=CH$_3$; $R^8$=H)[produced by Micromonospora echinospora ATCC 15837 (NRRL 2985), Micromonospora echinospora var. ferruginea ATCC 15836 (NRRL 2995), Micromonospora echinospora var. pallida ATCC 15838 (NRRL 2996) and Micromonospora purpurea ATCC 15835; U.S. Pat. Nos. 3,091,572 and 3,136,704], nebramycin factor 4 ($R^1$=CH$_2$NH$_2$; $R^2$=OH; $R^3$=OH; $R^4$=NH$_2$; $R^5$=NH$_2$; $R^6$=H; $R^7$=OH; $R^8$=CH$_2$OCONH$_2$) and factor 5' ($R^1$=CH$_2$NH$_2$; $R^2$=OH; $R^3$=H; $R^4$=NH$_2$; $R^5$=NH$_2$; $R^6$=H; $R^7$=OH; $R^8$=CH$_2$OCONH$_2$)[produced by Streptomyces tenebrarius ATCC 17920 and 17921; U.S. Pat. No. 3,691,279], sisomicin ($R^1$=CH$_2$NH$_2$; $R^2$=H; $R^3$=H; $R^4$=NH$_2$; $R^5$=NHCH$_3$; $R^6$=OH; $R^7$=CH$_3$; $R^8$=H; dotted line=the presence of double bond [produced by Micromonospora inyoensis ATCC 27600 (NRRL 3292); U.S. Pat. Nos. 3,907,771 and 3,832,286] and the like. Generic names of these compounds (II) and their substituents are listed in Table 1.

Table 1

| Generic Name | $R^1$ | $R^2$ | $R^3$ | $R^4$ | $R^5$ | $R^6$ | $R^7$ | $R^8$ | dotted line |
|---|---|---|---|---|---|---|---|---|---|
| tobramycin | CH$_2$NH$_2$ | OH | H | NH$_2$ | NH$_2$ | H | OH | CH$_2$OH | none |
| kanamycin A | " | " | OH | OH | " | " | " | " | " |
| kanamycin B | " | " | " | NH$_2$ | " | " | " | " | " |

Table 1-continued

| Generic Name | R¹ | R² | R³ | R⁴ | R⁵ | R⁶ | R⁷ | R⁸ | dotted line |
|---|---|---|---|---|---|---|---|---|---|
| kanamycin C | $CH_2OH$ | " | " | " | " | " | " | " | " |
| dideoxykanamycin B (dibekacin) | $CH_2NH_2$ | H | H | " | " | " | " | " | " |
| gentamicin C₁ | $CH(CH_3)NHCH_3$ | " | " | " | $NHCH_3$ | OH | $CH_3$ | H | " |
| gentamicin C₂ | $CH(CH_3)NH_2$ | " | " | " | " | " | " | " | " |
| gentamicin C₁ₐ | $CH_2NH_2$ | " | " | " | " | " | " | " | " |
| gentamicin B | " | " | OH | OH | " | " | " | " | " |
| nebramycin factor 4 | " | OH | " | $NH_2$ | $NH_2$ | H | OH | $CH_2OCONH_2$ | " |
| nebramycin factor 5' | " | " | H | " | " | " | " | " | " |
| sisomicin | " | H | " | " | $NHCH_3$ | OH | $CH_3$ | H | double bond |

In the aforementioned general formula (I), lower alkyl as R means $C_1$ to $C_5$ alkyl, particularly $C_1$ to $C_3$ alkyl, e.g. methyl, ethyl, propyl, isopropyl, butyl, isobutyl, sec-butyl; aralkyl means $C_7$ to $C_{10}$ aralkyl, e.g. benzyl, phenethyl, 1-phenylethyl, 3-phenylpropyl.

The novel aminoglycoside antibiotic derivatives (I) in this invention include the free bases and salts thereof, particularly non-toxic acid addition salts, for example, salts with inorganic acids such as hydrochloric acid, hydrobromic acid, hydroiodic acid, sulfuric acid, phosphoric acid, carbonic acid, and the like, and salts with organic acids such as acetic acid, dumaric acid, malic acid, tartaric acid, maleic acid, citric acid, mandelic acid, ascorbic acid, gallic acid, and the like.

Representative of the compounds (I) are:

(1) 1-N-(4-hydroxypiperidine-4-carboxyl)tobramycin
(2) 1-N-(4-hydroxypiperidine-4-carbonyl)kanamycin A
(3) 1-N-(4-hydroxypiperidine-4-carbonyl)kanamycin B
(4) 1-N-(4-hydroxypiperidine-4-carbonyl)kanamycin C
(5) 1-N-(4-hydroxypiperidine-4-carbonyl)dideoxykanamycin B
(6) 1-N-(4-hydroxypiperidine-4-carbonyl)gentamicin C₁
(7) 1-N-(4-hydroxypiperidine-4-carbonyl)gentamicin C₂
(8) 1-N-(4-hydroxypiperidine-4-carbonyl)gentamicin C₁ₐ
(9) 1-N-(4-hydroxypiperidine-4-carbonyl)gentamicin B
(10) 1-N-(4-hydroxypiperidine-4-carbonyl)nebramycin factor 4
(11) 1-N-(4-hydroxypiperidine-4-carbonyl)nebramycin factor 5'
(12) 1-N-(4-hydroxypiperidine-4-carbonyl)sisomicin
(13) 1-N-(3-hydroxypyrrolidine-3-carbonyl)tobramycin
(14) 1-N-(3-hydroxypyrrolidine-3-carbonyl)kanamycin A
(15) 1-N-(3-hydroxypyrrolidine-3-carbonyl)kanamycin B
(16) 1-N-(3-hydroxypyrrolidine-3-carbonyl)kanamycin C
(17) 1-N-(3-hydroxypyrrolidine-3-carbonyl)dideoxykanamycin B
(18) 1-N-(3-hydroxypyrrolidine-3-carbonyl)gentamicin C₁
(19) 1-N-(3-hydroxypyrrolidine-3-carbonyl)gentamicin C₂
(20) 1-N-(3-hydroxypyrrolidine-3-carbonyl)gentamicin C₁ₐ
(21) 1-N-(3-hydroxypyrrolidine-3-carbonyl)gentamicin B
(22) 1-N-(3-hydroxypyrrolidine-3-carbonyl)nebramycin factor 4
(23) 1-N-(3-hydroxypyrrolidine-3-carbonyl)nebramycin factor 5'
(24) 1-N-(3-hydroxypyrrolidine-3-carbonyl)sisomicin
(25) 1-N-(1-methyl-3-hydroxypyrrolidine-3-carbonyl)tobramycin
(26) 1-N-(1-methyl-3-hydroxypyrrolidine-3-carbonyl)kanamycin A
(27) 1-N-(1-methyl-3-hydroxypyrrolidine-3-carbonyl)kanamycin B
(28) 1-N-(1-methyl-3-hydroxypyrrolidine-3-carbonyl)kanamycin C
(29) 1-N-(1-methyl-3-hydroxypyrrolidine-3-carbonyl)dideoxykanamycin B
(30) 1-N-(1-methyl-3-hydroxypyrrolidine-3-carbonyl)gentamicin C₁
(31) 1-N-(1-methyl-3-hydroxypyrrolidine-3-carbonyl)gentamicin C₂
(32) 1-N-(1-methyl-3-hydroxypyrrolidine-3-carbonyl)gentamicin C₁ₐ
(33) 1-N-(1-methyl-3-hydroxypyrrolidine-3-carbonyl)gentamicin B
(34) 1-N-(1-methyl-3-hydroxypyrrolidine-3-carbonyl)nebramycin factor 4
(35) 1-N-(1-methyl-3-hydroxypyrrolidine-3-carbonyl)nebramycin factor 5'
(36) 1-N-(1-methyl-3-hydroxypyrrolidine-3-carbonyl)sisomicin
(37) 1-N-(1-isopropyl-3-hydroxypyrrolidine-3-carbonyl)tobramycin
(38) 1-N-(1-isopropyl-3-hydroxypyrrolidine-3-carbonyl)kanamycin A
(39) 1-N-(1-isopropyl-3-hydroxypyrrolidine-3-carbonyl)kanamycin B
(40) 1-N-(1-isopropyl-3-hydroxypyrrolidine-3-carbonyl)kanamycin C
(41) 1-N-(1-isopropyl-3-hydroxypyrrolidine-3-carbonyl)dideoxykanamycin B
(42) 1-N-(1-isopropyl-3-hydroxypyrrolidine-3-carbonyl)gentamicin C₁
(43) 1-N-(1-isopropyl-3-hydroxypyrrolidine-3-carbonyl)gentamicin C₂
(44) 1-N-(1-isopropyl-3-hydroxypyrrolidine-3-carbonyl)gentamicin C₁ₐ
(45) 1-N-(1-isopropyl-3-hydroxypyrrolidine-3-carbonyl)gentamicin B
(46) 1-N-(1-isopropyl-3-hydroxypyrrolidine-3-carbonyl)nebramycin factor 4
(47) 1-N-(1-isopropyl-3-hydroxypyrrolidine-3-carbonyl)nebramycin factor 5'
(48) 1-N-(1-isopropyl-3-hydroxypyrrolidine-3-carbonyl)sisomicin
(49) 1-N-(1-benzyl-3-hydroxypyrrolidine-3-carbonyl)tobramycin

(50) 1-N-(1-benzyl-3-hydroxypyrrolidine-3-carbonyl)-kanamycin A
(51) 1-N-(1-benzyl-3-hydroxypyrrolidine-3-carbonyl)-kanamycin B
(52) 1-N-(1-benzyl-3-hydroxypyrrolidine-3-carbonyl)-kanamycin C
(53) 1-N-(1-benzyl-3-hydroxypyrrolidine-3-carbonyl)-dideoxykanaycin B
(54) 1-N-(1-benzyl-3-hydroxypyrrolidine-3-carbonyl)-gentamicin $C_1$
(55) 1-N-(1-benzyl-3-hydroxypyrrolidine-3-carbonyl)-gentamicin $C_2$
(56) 1-N-(1-benzyl-3-hydroxypyrrolidine-3-carbonyl)-gentamicin $C_{1a}$
(57) 1-N-(1-benzyl-3-hydroxypyrrolidine-3-carbonyl)-gentamicin B
(58) 1-N-(1-benzyl-3-hydroxypyrrolidine-3-carbonyl)-nebramycin factor 4
(59) 1-N-(1-benzyl-3-hydroxypyrrolidine-3-carbonyl)-nebramycin factor 5'
(60) 1-N-(1-benzyl-3-hydroxypyrrolidine-3-carbonyl)-sisomicin
(61) 1-N-(1-ethyl-3-hydroxypyrrolidine-3-carbonyl)tobramycin
(62) 1-N-(1-ethyl-3-hydroxypyrrolidine-3-carbonyl)-kanamycin A
(63) 1-N-(1-ethyl-3-hydroxypyrrolidine-3-carbonyl)-kanamycin B
(64) 1-N-(1-ethyl-3-hydroxypyrrolidine-3-carbonyl)-kanamycin C
(65) 1-N-(1-ethyl-3-hydroxypyrrolidine-3-carbonyl)-dideoxykanamycin B
(66) 1-N-(1-ethyl-3-hydroxypyrrolidine-3-carbonyl)-gentamicin $C_1$
(67) 1-N-(1-ethyl-3-hydroxypyrrolidine-3-carbonyl)-gentamicin $C_2$
(68) 1-N-(1-ethyl-3-hydroxypyrrolidine-3-carbonyl)-gentamicin $C_{1a}$
(69) 1-N-(1-ethyl-3-hydroxypyrrolidine-3-carbonyl)-gentamicin B
(70) 1-N-(1-ethyl-3-hydroxypyrrolidine-3-carbonyl)nebramycin factor 4
(71) 1-N-(1-ethyl-3-hydroxypyrrolidine-3-carbonyl)nebramycin factor 5'
(72) 1-N-(1-ethyl-3-hydroxypyrrolidine-3-carbonyl)-sisomicin

II. PREPARATION

The compounds in this invention may readily be prepared by reacting said aminoglycosides (II) with carboxylic acids of the general formula (III):

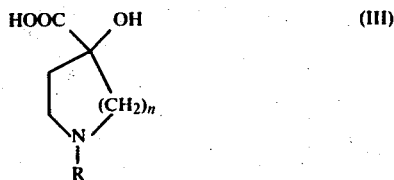
(III)

more particularly, they may be represented by the general formula:

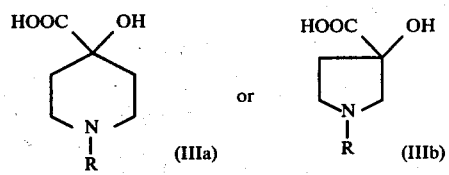

(wherein R and n have the same meaning as mentioned above) or their reactive derivatives.

Since the starting aminoglycosides have many functional groups (e.g. amino groups) other than the 1-amino group to be acylated, it is appropriate to optionally protect them by protecting groups. All of the protecting groups ordinarily used in peptide synthesis, which may readily be removed after acylation of 1-amino group, may be employed. Such groups include benzyloxycarbonyl which may optionally be substituted at the benzene nucleus, t-butyloxycarbonyl, t-amyloxycarbonyl, methoxycarbonyl, ethoxycarbonyl, tosyl(p-toluenesulfonyl), trityl, formyl, trifluoroacetyl, phthaloyl, m-nitrophenylthio, triphenylmethylthio and the like.

The reactive derivatives of the above mentioned carboxylic acids used as acylating agents include those ordinarily used in peptide synthesis, for example, acid halides, acid azides, acid anhydrides, mixed acid anhydrides, reactive esters and the like. Examples of these derivatives have been described in Synthesis 453(1972) and Peptide Synthesis 75 to 135(1966) by M. Bodanszky et al. In the acylating agents, when R is hydrogen atom, it is desirable to protect the skeletal nitrogen atom by a suitable protecting group, for example, the same ones as mentioned in the aminoglycoside protection. The acylating agents may easily be prepared in a conventional manner. For example, N-hydroxysuccinimido N-benzyloxycarbonyl-4-hydroxypiperidine-4-carboxylate may be prepared by reacting N-benzylpiperidone with hydrogen cyanide or potassium cyanide in dry tetrahydrofuran to yield N-benzylpiperidone cyanohydrin, hydrolyzing the latter with concentrated hydrochloric acid to yield the carboxylic acid derivative, debenzylating the latter by catalytic hydrogenation, reacting the latter with benzyloxycarbonyl chloride to yield N-benzyloxycarbonyl-4-hydroxypiperidine-4-carboxylic acid, and then esterifying the latter with N-hydroxysuccinimide. N-Hydroxysuccinimido N-benzyloxycarbonyl-3-hydroxypyrrolidine-3-carboxylate may be prepared in the same manner as mentioned above.

The acylation of aminoglycosides in this invention is achieved by reacting the starting materials, aminoglycosides, of which the functional groups other than the 1-amino group are protected, with the above acylating agent in a suitable solvent. In carrying out the acylation, an equimolar amount or an excess amount of acylating agent, preferably about 1.0 to 2.0 moles, is used to one mole of aminoglycosides. The reaction temperature is at 0° to 35° C., preferably 20° to 25° C.

Examples of the solvent employed are lower alcohols such as methanol, ethanol, and ethylene glycol, ethers such as diethyl ether, 1,2-dimethoxyethane, tetrahydrofuran, and dioxane, ketones such as acetone and methyl ethyl ketones, dimethylformamide, dimethylacetamide, pyridine, water, and the like, and they may be used alone or as a mixture of two or more kinds of them.

After the termination of acylation, the protecting groups are removed in conventional manners such as treatment with acids or catalytic hydrogenation to yield the objective compounds.

III. EFFECTS AND USE

The aminoglycoside antibiotic derivatives and the nontoxic salts thereof prepared in this invention exhibit excellent antimicrobial activities. They are several to several ten times more active than the corresponding unacylated aminoglycosides against some species of gram positive and negative bacteria. For example, Table 2 indicates comparatively minimum inhibitory concentrations (MIC, $\mu$g/ml) of 1-N-(4-hydroxypiperidine-4-carbonyl)tobramycin, tobramycin, gentamicin, sisomicin and kanamycin A. Table 3 indicates MIC ($\mu$g/ml) of 1-N-(3-hydroxypyrrolidine-3-carbonyl)tobramycin, tobramycin, 1-N-(3-hydroxypyrrolidine-3-carbonyl)kanamycin A and kanamycin A.

ing the growth of bacteria alive in perishables, feedstuffs, or hygenical materials.

The compounds (I) in this invention can be used in a wide variety of oral or parenteral dosage forms solely or in admixture with other co-acting substances. The pharmaceutical compositions may be a mixture of 0.01 to 99% of the compounds (I) with a pharmaceutical carrier or carriers which can be a solid material or liquid material in which the compounds (I) are soluble, dispersible, or suspensible. They can be in a unit dosage form. The solid compositions can be in forms of tablets, powder, dry syrups, troches, granules, capsules, pills, suppositories, or like solid preparations. The liquid compositions can be in forms of injections, ointments, dispersions, inhalant, suspensions, solutions, emulsions, syrups, or elixirs. All of diluents (e.g. starch, sucrose, lactose, calcium carbonate, kaolin); bulking agents (e.g.

Table 2

MIC of [1]TOB derivative, [2]TOB, [3]GM, [4]SSM, and [5]KM-A ($\mu$g/ml)

| Bacteria | TOB der. | TOB | GM | SSM | KM-A |
|---|---|---|---|---|---|
| seudomonas aeruginosa PP-6* | 6.25 | 50 | >200 | 200 | 200 |
| Pseudomonas aeruginosa TM-121* | 12.5 | 100 | 100 | 200 | >200 |
| Pseudomonas aeruginosa TB-151* | 6.25 | 100 | 100 | >200 | >200 |
| Staphylococcus aureus ATCC 25923 | 1.56 | 1.56 | 0.78 | 1.56 | 6.25 |
| Escherichia coli W-677/JR 762* | 6.25 | 100 | 100 | 50 | >200 |
| Escherichia coli W-677/JR 214* | 1.56 | 50 | 100 | 25 | >200 |
| Klebsiella pneumoniae Kl-38 | 1.56 | 3.13 | 0.78 | 0.39 | >200 |
| Proteus mirabilis TB-617 | 6.25 | 12.5 | 25 | 12.5 | >200 |
| Proteus vulgaris TB-162* | 6.25 | 12.5 | 6.25 | 12.5 | >200 |

Note:
[1]TOB derivative means 1-N-(4-hydroxypiperidine-4-carbonyl)-tobramycin.
[2]TOB means tobramycin.
[3]GM means gentamicin.
[4]SSM means sisomicin.
[5]KM-A means kanamycin A.
*shows tobramycin resistant organisms.

Table 3

MIC of [1]TOB derivative, [2]TOB, [3]KM-A derivative and [4]KM-A ($\mu$g/ml)

| Bacteria | TOB der. | TOB | KM-A der. | KM-A |
|---|---|---|---|---|
| Staphylococcus aureus 80285 | 0.39 | 0.78 | 12.5 | >100 |
| Escherichia coli TB-705 | 3.13 | 6.25 | 25 | >100 |
| Escherichia coli W-677/JR 214* | 0.78 | 100 | 6.25 | >100 |
| Klebsiella pneumoniae Kl-38 | 0.78 | 1.56 | 3.13 | >100 |
| Enterobacter cloacae CI-83 | 0.78 | 0.78 | 3.13 | >100 |
| Serratia marcescens MA-26* | 12.5 | 50 | 6.25 | >100 |
| Citrobacter freundii Ct-31 | 0.78 | 3.13 | 3.13 | >100 |
| Proteus mirabilis TB-617 | 1.56 | 12.5 | 6.25 | >100 |
| Proteus vulgaris TB-162* | 1.56 | 6.25 | 3.13 | >100 |
| Proteus rettgeri Ret 33 | 0.78 | 1.56 | 1.56 | >100 |
| Pseudomonas aeruginosa PP-6* | 3.13 | >100 | 12.5 | >100 |
| Pseudomonas aeruginosa TB-151* | 3.13 | 100 | 6.25 | >100 |

Note:
[1]TOB derivative means 1-N-(3-hydroxypyrrolidine-3-carbonyl)-tobramycin.
[2]TOB means tobramycin.
[3]KM-A derivative means 1-N-(3-hydroxypyrrolidine-3-carbonyl)-kanamycin A.
[4]KM-A means kanamycin A.
*shows tobramycin resistant organisms.

As seen from Tables 2 and 3, the compounds (I) in this invention are valuable antimicrobial agents effective against various species of gram positive and negative bacteria, and useful as drugs used for humans and other verious kind of animals. They can be used in prevention or treatment of infections caused by gram positive bacteria (e.g. *Staphylococcus aureus, Bacillus anthracis*) and gram negative bacteria (e.i. *Escherichia coli, Klebsiella pneumoniae, Proteus mriabilis, Proteus vulgaris, Pseudomonas aeruginosa*). The compounds (I) in this invention can also be used as disinfectants for preventlactose, sugar, salt, glycine, starch, calcium carbonate, calcium phosphate, kaolin, bentonite, talc, sorbitol); binders (e.g. starch, acacia, gelatin, glucose, sodium arginate, tragacanth, carboxymethylcellulose, sorbitol, polyvinylpyrrolidone); disintegrators (e.g. starch, agar, carbonates, sodium laurylsulfate), lubricant (e.g. stearic acid, talc, paraffin, boric acid, sillica, sodium benzoate, polyethylene glycol, cacao oil, magnesium sulfate); emulsifying agents (e.g. lecithin, sorbitan monooleate, acacia); suspending agents (e.g. sorbitol, methylcellulose, glucose, sugar syrup, gelatin, hydroxyethylcellulose, carboxymethylcellulose, aluminum stearate gel, hydrogenated fats); solvents (e.g. water, peanut oil, sesame oil, methyl oleate); preservatives (e.g. methyl or ethyl p-hydroxybenzoate, sorbic acid), edible coloring agents, aromatic substances, solubilizing agents, buffers, stabilizing agents, dispersing agents, wetting agents, antioxidants, and the like can be used in the conventional manners as far as they do not act adversely on the compounds (I).

The compounds (I) in this invention, particularly, their sulfates, are readily soluble in water and conveniently used as solutions for intravenous, intramusclar, or subcutaneous injections according to a conventional method. The compounds (I) can be dissolved in aqueous or oily solvents for injection to give an injectable solution in an ampoule; in order to preserve the injectable preparation for a long period of time, it is appropriate to make a vial preparation containing crystalline, powder, microcrystalline, or lyophilizate of the compounds (I). The vial preparation may be dissolved or suspended in the said solvents for injection immediately before use. The preparation may contain said preservatives.

Further, the compounds (I) in this invention can be used as suppositories, ointments for topical or opthalmic use, powders for topical use, and like preparations preparable according to the methods well known to those skilled in the art. The external preparation can contain 0.01 to 99% of the compounds (I) in this invention together with a necessary amount of pharmaceutical carrier given above.

This invention also provides a method for treating or preventing infections caused by bacteria in humans or domestic animals, which comprises administering to the human or animal the compounds (I) in this invention at a devided or single dose of 0.01 to 5 g/kg a day for injection or 0.01 to 10 g/kg a day for oral administration, or 0.01 to 10 g a day for a topical application at intervals of 3 to 12 hours.

The method is applicable for treating or preventing some infectious diseases caused by bacteria sensitive to the compounds in this invention, e.g. staphylodermia, anthropozoonosis, cystitis, pyelitis, pneumonia, pneumonitis, bronchitis, empyematic nasopharyngitis, tonsillitis, rhinitis, dermatitis, pustulosis, abscess, wound and soft tissue infections, ear infections, osteomyeltitis, septicemia, enteritis, urinary tract infections, and pyelonephritis.

Preferably, the compounds (I) in this invention are given to a patient in forms of pharmaceutical preparation, e.g. powder, dry syrup, tablets, troches, granules, capsules, pills, suppositories, injections, ointments, dispersions, inhalant, suspensions, solutions, emulsions, syrups and elixirs. They may be in a unit dosage form, e.g. tablets, troches, capsules, injections, vials, granules or powder in a separate container of package.

The following examples are provided to further illustrate this invention.

EXAMPLE 1

Preparation of N-hydroxysuccinimido N-benzyloxycarbonyl-4-hydroxypiperidine-4-carboxylate (a) To a solution of 10.0 g (53 mmoles) of N-benzylpiperidone in 14 ml of dry tetrahydrofuran is added 23 ml (3.6 equivalents) of 25% (by weight; the same applies correspondingly to the followings) solution of hydrogen cyanide in tetrahydrofuran at room temperature, and the mixture allowed to stand for 1 hour. The solvent and residual reactants are removed by evaporation under reduced pressure to yield 11.50 g of N-benzylpiperidone cyanohydrin as a colorless crystalline compound, mp. 79°–95° C.

(b) A mixture of 9.477 g (43.9 mmoles) of the crude N-benzylpiperidone cyanohydrin prepared above and 18.4 ml (5 equivalents) of concentrated hydrochloric acid is heated on a water bath for 1 hour. Ammonium chloride is precipitated as crystalline in the course of the reaction. The reaction mixture is cooled, and the precipitated ammonium chloride is collected by filtration and washed with cold acetone. The combined filtrate and washings are evaporated to dryness under reduced pressure to yield 12.65 g of residue.

The residue is dissolved in 65 ml of water, mixed with 28 ml of water containing 3.97 g of sodium acetate, and the mixture is evaporated under reduced pressure. The resulting residue is triturated with 150 ml of acetone and the insoluble material extracted with a mixture of chloroform and methanol (9:1). The insoluble sodium chloride is filtered off, and the filtrate is evaporated under reduced pressure. The resulting residue is dissolved in 46 ml of water, mixed with acetone, and the mixture is kept in a refrigerator overnight. The precipitated crystalline are collected by filtration and washed with cold acetone to yield 8.70 g of N-benzyl-4-hydroxypiperidine-4carboxylic acid (84.5% yield), mp. 260.5°–262° C. (decomposition). The crystalline contain one mole of water of crystallization, which is lost when dried at 75° C. under reduced pressure for 5 hours. The weight decreases to 7.92 g (77% yield).

(c) A solution of 2.35 g (10 mmoles) of the above prepared N-benzyl-4-hydroxypiperidine-4-carboxyic acid dissolved in a mixture of 20 ml of water, 20 ml of methanol, and 2.0 ml of concentrated hydrochloric acid is catalytically hydrogenated in hydrogen atmosphere for 23 hours in the presence of 1 g of 10% palladium-charcoal. After termination of the reaction, the catalyst is removed off by filtration and washed with aqueous methanol. The combined filtrate and washings are evaporated under reduced pressure to yield 1.95 g of residue as light yellow crystalline.

This is dissolved in 15 ml of water containing 1.25 g (30 mmoles) of sodium hydroxide, and 2.05 g (12 mmoles) of benzyloxycarbonyl chloride is added thereto over a period of 30 minutes at room temperature with stirring. The mixture is allowed to stand at room temperature for 2 hours, and 0.5 ml of 10% aqueous solution of sodium hydroxide is added. The mixture is washed with ether and the aqueous layer is adjusted to pH 2 with 10% hydrochloric acid to yield an oily material, which is extracted with ether. The ethereal solution is washed with water and dried over anhydrous sodium sulfate to yield 2.53 g (90% yield) of N-benzyloxycarbonyl-4-hydroxypiperidine-4-carboxylic acid as a light yellow oily material.

IR: $\nu_{max}^{CHCl_3}$ (cm$^{-1}$): 3500 to 2400, 1730, 1700.

(d) To a suspension of 2.49 g (8.92 mmoles) of the abovementioned N-benzyloxycarbonyl-4-hydroxypiperidine-4-carboxylic acid and 1.02 g (8.92 mmoles) of N-hydroxysuccinimide in 40 ml of dry ethyl acetate is added a solution of 1.83 g (8.92 mmoles) of dicyclohexylcarbodiimide in 5 ml of dry ethyl acetate, and the mixture stirred at room temperature overnight and then cooled in an ice bath. The insoluble material is removed by filtration and washed with cold ethyl acetate. The combined filtrate and washings are evaporated under reduced pressure to yield 3.34 g of N-hydroxysuccinimido N-benzyloxycarbonyl-4-hydroxypiperidine-4-carboxylate (quantitative yield).

IR: $\nu_{max}^{CHCl_3}$ (cm$^{-1}$): 3500, 1820, 1790, 1700, 1690. This is used in the subsequent acylation without further purification.

EXAMPLE 2

Preparation of N-hydroxysuccinimido DL-1-benzyloxycarbonyl-3-hydroxypyrrolidine-3-carboxylate (a) To a solution of 16.40 g (9.45 mmoles) of 1-benzyl-3-pyrrolidone (see E. Jaeger and J. H. Biel; J. Org. Chem., 30, 740 to 744 (1975)) in 5 ml of tetrahydrofuran is added 40 ml (343 mmoles) of 25% HCN/tetrahydrofuran solution, and the mixture allowed to stand for 5 hours. The solvent and excess of the reagent are evaporated under reduced pressure. The residue is dissolved in 38.5 ml of concentrated hydrochloric acid and the solution heated on a water bath for 1 hour. After cooling, the precipitated ammonium chloride is filtered off and washed with 4 ml of cold concentrated hydrochloric acid and then with acetone. The combined filtrate and washings are evaporated under reduced pressure. The residue is dissolved in 50 ml of an aqueous solution of 8 g of sodium acetate, and the mixture (pH 5) is evaporated under reduced pressure. The residue is dissolved in chloroform, and the insoluble sodium chloride is removed by filtration and washed with chloroform. The chloroform layer is extracted with 50 ml of aqueous solution of 4 g of sodium hydroxide (the mixture becomes pH 9). The aqueous layer is washed once with chloroform, slowly adsorbed on 200 ml of Amberlite IR-120B (H$^+$) (at a speed of 3 to 4 seconds per one drop). The column is washed with 400 ml of water, and eluted with 700 ml of 1 N-ammonium hydroxide. The eluate is evaporated under reduced pressure, and the resulting residue is recrystallized from 80 ml of water to yield 12.084 g of colorless needles, mp. 184°–189° C. (decomposition). The needles contain water of crystallization, which is removed at 70° C. under reduced pressure for 2 days to yield 10.45 g of DL-1-benzyl-3-hydroxypyrrolidine-3-carboxylic acid (50.0% yield).

Elemental analysis: (for $C_{12}H_{15}NO_3 \cdot 1/5 H_2O$)—Calcd (%): C, 64.10; H, 6.90; N, 6.23. Found (%): C, 64.10; H, 6.94; N, 6.25.

IR: $\nu_{max}^{Nujol}$ (cm$^{-1}$): 1601 (strong).

(b) To a solution of 885 mg (4.0 mmoles) of DL-1-benzyl-3-hydroxypyrrolidine-3-carboxylic acid dissolved in 50% aqueous dioxane is added 1 ml of concentrated hydrochloric acid, and the mixture is catalytically hydrogenated in the presence of 440 mg of 10% palladium-charcoal. The catalyst is removed off by filtration and washed with aqueous dioxane. The combined filtrate and washings are evaporated under reduced pressure to yield the residue, which is crystallized from acetone to yield 610 mg of DL-3-hydroxypyrrolidine-3-carboxylic acid hydrochloride as colorless prisms (91% yield), mp. 201°–210° C. (decomposition).

(c) To a solution of 610 mg (3.6 mmoles) of DL-3-hydroxypyrrolidine-3-carboxylic acid hydrochloride dissolved in 10 ml of water is added 6 ml of an aqueous solution of 456 mg (3 equivalents) of sodium hydroxide and 750 mg (1.2 equivalents) of benzyloxycarbonyl chloride at room temperature with stirring, and the mixture is stirred for 2 hours. The reaction mixture is adjusted to pH 11 with 10% aqueous sodium hydroxide solution, washed twice with ether, then adjusted to pH 2 with 10% hydrochloric acid, and extracted thrice with ether. The extract is dried over anhydrous sodium sulfate and evaporated under reduced pressure to yield 800 mg of the residue, which is crystallized from a mixture of ether and petroleum ether. The resulting crystals (mp. 117°–133° C.) are recrystallized from a mixture of ether and methylene chloride to yield 595 mg of DL-1-benzyloxycarbonyl-3-hydroxypyrrolidine-3-carboxylic acid (61.6% yield), mp. 142°–144° C.

Elemental analysis: (for $C_{13}H_{15}NO_5$)—Calcd (%): C, 58.86; H, 5.70; N, 5.28. Found (%): C, 58.96; H, 5.76; N, 5.16.

IR: $\nu_{max}^{Nujol}$ (cm$^{-1}$): 3230, 1750, 1680.

(d) To a solution of 266 mg (1.0 mmole) of DL-1-benzyloxycarbonyl-3-hydroxypyrrolidine-3-carboxylic acid dissolved in 30 ml of ethyl acetate with warming is added 115 mg (1.0 mmole) of powdered N-hydroxysuccinimide. Colorless crystals are deposited immediately after addition of 206 mg (1.0 mmole) of dicyclohexylcarbodiimide. The mixture is stirred for 1.5 hours and kept in a refrigerator overnight. The crystallines are collected by filtration, and the insoluble material is washed with ethyl acetate. The combined filtrate and washings are evaporated under reduced pressure to yield 390 mg of the residue (mp. 154°–161° C.). This is recrystallized from a mixture of acetone and hexane to yield 277 mg of N-hydroxysuccinimido DL-1-benzyloxycarbonyl-3-hydroxypyrrolidine-3-carboxylate (76.5% yield), mp. 159°–161° C.

IR: $\nu_{max}^{Nujol}$ (cm$^{-1}$): 3350, 1815, 1785, 1740, 1690.

EXAMPLE 3

Preparation of 1-N-(4-hydroxypiperidine-4-carbonyl)kanamycin A

To a solution of 1.55 g (2.5 mmoles) of 6'-N-t-butoxycarbonyl-kanamycin A (see Japanese Patent Unexamined Publication No. 50-140420) in 24 ml of 50% 1,2-dimethoxyethane is dropwise added a solution of 1.53 g (4.06 mmoles) of N-hydroxysuccinimido N-benzyloxycarbonyl-4-hydroxypiperidine-4-carboxylate in 24 ml of 1,2-dimethoxyethane at 2° to 3° C. over a period of 2 hours. The mixture is stirred at room temperature for 14.5 hours and evaporated under reduced pressure at a bath temperature bellow 35° C. to yield 3.2 g of the residue as white foamy material. This is dissolved in 20 ml of 90% trifluoroacetic acid, and the mixture is allowed to stand at room temperature for 1¾ hours and evaporated under reduced pressure. The residue is dissolved in 50 ml of 50% aqueoues methanol and catalytically hydrogenated in the presence of 1 g of 10% palladium-charcoal under hydrogen atmosphere for 3 hours. After termination of the reaction, the palladium-charcoal is removed by filtration, and the solvent is evaporated under reduced pressure. The residue (4.15 g) is dissolved in 10 ml of water, adsorbed on 100 ml of Amberlite CG-50 (NH$_4^+$), and the column is washed with 240 ml of water, and eluted with 1000 ml of water and 1000 ml of 1 N-ammonium hydroxide by the Gradient method (one fraction: 10 g).

The eluates (475 mg) from fraction Nos. 91 to 108 are dissolved in 10 ml of water, adsorbed on 100 ml of Amberlite CG-50 (NH$_4^+$), and the column is washed with 20 ml of water, and eluted with 1000 ml of water and 1000 ml of 1 N-ammonium hydroxide.

The eluates (270 mg) from fraction Nos. 89 to 95 are dissolved in 6 ml of water, adsorbed on a column of 100 ml of Amberlite CG-50 (NH$_4^+$), and the column is washed with 30 ml of water, and eluted with 1000 ml of water and 1000 ml of 1 N-ammonium hydroxide. The eluate (270 mg) from fraction Nos. 89 to 95 are dissolved in 6 ml of water, adsorbed on a column of 100 ml of Amberlite CG-50 ($NH_4^+$), and the column is washed with 30 ml of water, and eluted with 1000 ml of water, and 0.5 N-ammonium hydroxide. The eluates from fraction Nos. 159 to 166 are lyophilized to yield 71 mg of the objective compound (6% yield).

$[\alpha]_D^{24} + 86.3° \pm 1.2°$ (c=1.016, $H_2O$)

TLC (Kieselgel 60 $F_{254}$; Merck): Rf=0.45 [Solvent system/methanol:concentrated ammonia (1:1)] (cf. kanamycin A: Rf=0.25)

EXAMPLE 4

Preparation of 1-N-(4-hydroxypiperidine-4-carbonyl)tobramycin (a) To a solution of 9.0 g (17.9 mmoles) of tobramycin dihydrate in 322 ml of water are added 322 ml of pyridine, 32 ml of triethylamine and 2.64 g (18.4 mmoles) of t-butyloxycarbonylazide, and the mixture is allowed to stand at room temperature overnight and evaporated under reduced pressure at 40° C. The resulting product is dissolved in 100 ml of water, and the mixture is evaporated under reduced pressure. This operation is repeated thrice to yield 11.95 g of the residue.

The residue is dissolved in 60 ml of water, and adsorbed on 450 ml of Amberlite CG-50 ($NH_4^+$). The column is washed with 1500 ml of water and eluted with 1000 ml of water and 1000 ml of 0.1 N-ammonium hydroxide by the Gradient method, and then with 4100 ml of 0.1 N-ammonium hydroxide (one fraction: 15 g). Fraction Nos. 141 to 200 yield 4.70 g of 6'-N-t-butyloxycarbonyl-tobramycin (46.4% yield).

$[\alpha]_D^{23.5} + 110.3° \pm 1.6°$ (c=0.940, $H_2O$)

Elemental analysis: (for $C_{23}H_{45}N_5O.\frac{1}{2}H_2O$)—Calcd (%): C, 47.90; H, 8.00; N, 12.15. Found (%): C, 47.79; H, 7.92; N, 11.78.

(b) To a solution of 1.81 g (3.0 mmoles) of the above-prepared 6'-N-t-butyloxycarbonyl-tobramycin dissolved in a mixture of 5 ml of water and 5 ml of dimethylformamide is dropwise added 8 ml of dimethylformamide solution containing 0.748 g (3.0 mmoles) of N-benzyloxycarbonylsuccinimide at 0° to 5° C. with stirring over a period of 2 hours, and the mixture is stirred at the same temperature overnight.

Solvent is evaporated under reduced pressure to yield 3.17 g of the residue. This is dissolved in 40 ml of water and extracted four times with each 30 ml of ethyl acetate. The aqueous layer is adsorbed on 100 ml of Amberlite CG-50 ($NH_4^+$), and eluted with 1700 ml of water and 1700 ml of 0.05 N-ammonium hydroxide by the Gradient method and then with 1500 ml of 0.01 N-ammonium hydroxide (one fraction: 18 ml).

The fraction Nos. 13 to 132 yield 877 mg of 6'-N-t-butyloxycarbonyl-2'-N-benzyloxycarbonyltobramycin (40% yield). Fraction Nos. 114 to 132 are lyophilized and the physical properties are measured.

$[\alpha]_D^{25} + 87.2° \pm 1.2°$ (c=1.023, $H_2O$)

Elemental analysis: (for $C_{31}H_{51}N_5O_{13}.1.5H_2O$)—Calcd (%): C, 51.09; H, 7.47; N, 9.61. Found (%): C, 51.09; H, 7.47; N, 9.37.

IR: $\nu_{max}^{KBr}$ ($cm^{-1}$): 3355, 1697.

TLC (Kieselgel 60 $F_{254}$; Merck): Rf=0.19 [Solvent system/isopropyl alcohol:concentrated aqueous ammonia:chloroform (4:1:1)] (cf. 6'-N-t-butyloxycarbonyl-tobramycin: Rf=0.08)

(c) To a solution of 397 mg (0.566 mmole) of 6'-N-t-butyloxycarbonyl-2'-N-benzyloxycarbonyl-tobramycin dissolved in 50% aqueous dimethylformamide is dropwise added a solution of 319 mg (0.679 mmole) of N-hydroxysuccinimide N-benzyloxycarbonyl-4-hydroxypiperidine-4-carboxylate in 6 ml of dimethylformamide at 0° to 3° C. with stirring over a period of 1⅜ hours. The mixture is stirred at the same temperature for 50 minutes and then at room temperature for 4 hours, and evaporated under reduced pressure to yield 787 mg of the residue as colorless foamy material. This is dissolved in 8 ml of 90% trifluoroacetic acid, and the mixture is stirred at room temperature for 1.5 hours and evaporated to yield residue, which is catalytically hydrogenated with 334 mg of 5% palladium-charcoal in a mixture of 3 ml of acetic acid, 0.6 ml of water and 3 ml of methanol. After termination of the reaction, the catalyst is filtered off, and the filtrate is evaporated under reduced pressure to yield 1.25 g of residue. This is dissolved in 4 ml of water and adsorbed on a column of 30 ml of Amberlite CG-50 ($NH_4^+$). The column is washed with 300 ml of water, and eluted with 1000 ml of water and 1000 ml of 1 N-ammonium hydroxide by the Gradient method (one fraction: 10 ml).

The eluates (47 mg) of fraction Nos. 68 to 73 are dissolved in 1.5 ml of water, adsorbed on 5 ml of Amberlite CG-50 ($NH_4^+$) and eluted with 480 ml of water and 480 ml of 1 N-ammonium hydroxide by the Gradient method (one fraction: 5 ml).

The eluates of fraction Nos. 40 to 43 are lyophilized to yield 16 mg of the objective compound (4.9% yield).

TLC (Kieselgel 60 $F_{254}$; Merck): Rf=0.35 [Solvent system/methanol:concentrated aqueous ammonia (1:1)] (cf. tobramycin: Rf=0.58)

EXAMPLE 5

Preparation of DL-1-N-(3-hydroxypyrrolidine-3-carbonyl)tobramycin (a) A mixture of 174 mg (0.3 mmole) of tetra-N-formyltobramycin [prepared in accordance with the method described in Japanese Patent Unexamined Publication No. 50-35129] and 131 mg (1.2 equivalents) of N-hydroxysuccinimido DL-1-benzyloxycarbonyl-3-hydroxypyrrolidine-3-carboxylate dissolved in 10 ml of dimethylformamide is allowed to stand at room temperature for 2 hours and then evaporated under reduced pressure to yield residue, which is triturated well with ethyl acetate. The precipitate, which appears, is collected by filtration, and washed with ethyl acetate. The residue (266 mg) is hydrogenated with 140 mg of 10% palladium-charcoal in a mixture of 10 ml of water, 8 ml of methanol and a drop of acetic acid. After removal of the catalyst, 204 mg of crude tetra-N-formyl-DL-1-N-(3-hydroxypyrrolidine-3-carbonyl)tobramycin is obtained.

(b) Hydrolysis of tetra-N-formyl-DL-1-N-(3-hydroxypyrrolidine-3-carbonyl)tobramycin (i) With 5% hydrochloric acid and methanol To a solution of 204 mg of tetra-N-formyl-DL-1-N-(3-hydroxypyrrolidine-3-carbonyl)tobramycin prepared above in 0.22 ml of water is added 1.96 ml of 5% hydrochloric acid: methanol solution (a mixture of 0.55 ml of concentrated hydrochloric acid and 6 ml of methanol), and the mixture is hydrolyzed at 36° C. on an oil bath for 22.5 hours. After termination of the reaction, the excess amount of hydrochloric acid is removed on treatment with 6 ml of Amberlite IR-45. The resin is removed by filtration and washed with water. The combined filtrate and washings are evaporated under reduced pressure to yield 197 mg of residue. The residue is chromatographed on a column of 25 ml of Amberlite CG-50 ($NH_4^+$) and eluted with 500 ml of water and 500 ml of 1 N-ammonium hydroxide by the Gradient method. Eluates of fraction Nos. 64 to 78 are condensed and lyophilized to yield 98 mg of DL-1-N-(3-hydroxypyrrolidine-3-carbonyl)tobramycin (yield as biscarbonate: 46.4%).

$[\alpha]_D^{24} + 85.2° \pm 1.2°$ (c=1.046, $H_2O$)

TLC (Kieselgel 60 $F_{254}$; Merck): Rf=0.40 [Solvent system/isopropyl alcohol:concentrated aqueous ammonia (1:1)] (cf. tobramycin: Rf=0.56)

(ii) With hydrazine hydrate-acetic acid

A solution (pH 6) of 206 mg of the above-prepared tetra-N-formyl-DL-1-N-(3-hydroxypyrrolidine-3-carbonyl)tobramycin dissolved in a mixture of 20 ml of hydrazine monohydrate and 2.63 ml of acetic acid is refluxed with stirring for 6 hours. The reaction mixture is diluted with water to 400 ml, adsorbed on 100 ml of Amberlite CG-50 ($NH_4^+$), washed with 1 L of water and 1 L of 0.4% ammonium hydroxide, and then eluted with 0.8% ammonium hydroxide (one fraction: 12 ml).

Fraction Nos. 20 to 47 are evaporated under reduced pressure and lyophilized to yield 125 mg of the objective compound (yield as $3H_2CO_3$ salt: 54.6%).

$[\alpha]_D^{24} + 77.0° \pm 1.1°$ (c=1.064, $H_2O$)

Elemental analysis: (for $C_{23}H_{44}N_6O_{11}.3H_2CO_3$)—Calcd (%): C, 40.75; H, 6.57; N, 10.96. Found (%): C, 40.62; H, 6.39; N, 10.80.

This compound is identical with an authentic specimen prepared in method i.

EXAMPLE 6

Preparation of 1-N-(1-ethyl-3-hydroxypyrrolidine-3-carbonyl)tobramycin

A mixture of 1-benzyloxycarbonyl-3-hydroxypyrrolidine-3-carboxylic acid (2.090 g; 7.16 mmoles), 3,2',6',3''-tetra-N-formyl-tobramycin (4.160 g; 7.16 mmoles), N-hydroxysuccinimide (910 mg) and dicyclohexylcarbodiimide (1.870 g; 7.16 mmoles) dissolved in 50 ml of N,N-dimethylformamide is allowed to stand at room temperature overnight. The precipitated dicyclohexylurea is filtered off and washed with 5 ml of N,N-dimethylformamide. To the combined filtrate and washing, 550 mg of ethyl acetate is added to yield a precipitate. The precipitate is collected by filtration, washed with ethyl acetate, dissolved in water, and evaporated under reduced pressure. The residue (6.00 g) is dissolved in a mixture of 70 ml of water and 20 ml of methanol, and catalytically hydrogenated in the presence of 2.00 g of 10% palladium-charcoal under hydrogen atmosphere. After a calculated amount of hydrogen gas is absorbed, the catalyst is filtered off and washed with water. The combined filterate and washing are evaporated under reduced pressure to yield 5.30 g of 1-N-(3-hydroxypyrrolidine-3-carbonyl)-3,2',6',3''-tetraformyl-tobramycin as colorless powder.

To a solution of 228 mg (0.3 mmole) of the powder dissoved in 0.5 ml of water is added 1.0 ml of acetonitrile. The mixture is separated into two layers and then becomes homogenous on addition of 0.48 ml of an aqueous solution of acetaldehyde freshly distilled (a solution of 6.77 g acetaldehyde in 50 ml of water).

Immediately, 30 mg of sodium cyanoborohydride is added while adjusting the mixture to pH 7 with acetic acid. After 2 hours, the mixture is concentrated, and to the residue, 4 ml of ethyl acetate is added, and the mixture is agitated well. The resulting powder is collected by filtration, washed with ethyl acetate, dissolved in a mixture of 1 ml of water and 1 ml of isopropyl alcohol, slowly adsorbed on a column of 13.5 g of Kieselgel 60 (prepared by Merck Co.), and eluted with a mixture of isopropyl alcohol, concentrated ammonium hydroxide and chloroform (2:1:1) (one fraction: 10 g). The eluates from Fraction Nos. 11 to 30 are evaporated, and the residue (138 mg) is dissolved in 14.6 ml of water, to which 1.46 ml of hydrazine hydrate and 1.73 ml of acetic acid are added. The mixture is refluxed for 6 hours, diluted with 261 ml of water and adsorbed on 73 ml of Amberlite CG-50 ($NH_4^+$ type). The column is washed with 680 ml of water, and then eluted with 0.4% aqueous ammonium hydroxide solution (one fraction; 10 g).

The eluate from Fraction Nos. 70 to 75 is treated with decolorizing carbon, and the mixture is filtered through a pyrex filter for microanalysis (made by Nihon Millipore Ltd.), and the filtrate is evaporated to yield 52.2 mg of the title compound as colorless powder.

This is dissolved in a small amount of water, adjusted to pH 4.6 with 0.0955 N-sulfuric acid and evaporated under reduced pressure. Ethanol is added, and the precipitate, which appears, is collected by filtration, washed with ethanol, dissolved in water, treated with decolorizing carbon (Norit A), filtered through a pyrex filter for microanalysis (made by Nihon Millipore Ltd.) and lyophilized to yield 103 mg of the corresponding sulfate (41.9% overall yield).

$[\alpha]_D^{25} + 72.5° \pm 1.1°$ (c=1.031, in $H_2O$)

Elemental analysis (for $C_{25}H_{48}N_6O_{11}.2.5H_2SO_4.10.5H_2O$)—Calcd (%): C, 28.79; H, 7.15; N, 8.06; S, 7.69. Found (%): C, 28.61; H, 6.93; N, 7.93; S, 7.48.

The following compounds in Table 4 may be prepared in the same manners as described above.

Table 4

| Product | Yield (%) | Specific Rotation | Elemental Analysis | NMR: $\delta_{ppm}^{D2O}$ |
|---|---|---|---|---|
| 1-N-(1-Methyl-3-hydroxypyrrolidine-3-carbonyl)tobramycin sulfate | 31.3 | $[\alpha]_D^{23.0} = +74.4° \pm 1.1$ (c=1.041 in $H_2O$) | (for $C_{24}H_{46}N_6O_{11}.2.OH_2SO_4.4H_2O$) Calcd (%): C,33.40 ; H,6.78 ; N, 9.74 ; S,7.43. Found (%): C,32.98 ; H,6.43 ; N, 9.78 ; S,7.86. | 3.56s, 6.37d(aromatic H), 5.67m. |
| 1-N-(1-Isopropyl-3-hydroxy-pyrrolidine-3-carbonyl)tobramycin sulfate | 24.2 | $[\alpha]_D^{22.0} = +73.0° \pm 1.1$ (c=1.010 in $H_2O$) | (for $C_{26}H_{50}N_6O_{11}.2.5H_2SO_4.3H_2O$) Calcd (%): C,34.05 ; H,6.16 ; N, 9.17 ; S,8.74. | 1.83d(aromatic H), 6.37d, 5.67m. |

Table 4-continued

| Product | Yield (%) | Specific Rotation | Elemental Analysis | NMR: $\delta^{D_2O}_{ppm}$ |
|---|---|---|---|---|
| | | | Found (%): C,34.02; H,6.79; N, 9.11; S,8.63. | |
| 1-N-(1-Benzyl-3-hydroxypyrrolidine-3-carbonyl)tobramycin sulfate | 57.0 | $[\alpha]_D^{22.0} = +70.6° \pm 1.1$ (c=0.999 in H$_2$O) | (for C$_{30}$H$_{50}$N$_6$O$_{11}$.2.5H$_2$SO$_4$.2.5H$_2$O) Calcd (%): C,37.49; H,6.29; N, 8.75; S,8.34. Found (%): C,37.82; H,6.35; N, 8.54; S,7.91. | 8.01s, 4.98s, 6.34d, 5.82m. |
| 1-N-(3-Hydroxypyrrolidine-3-carbonyl)kanamycin A sulfate | 69.6 | $[\alpha]_D^{24.0} = +75.7° \pm 1.1$ (c=1.046 in H$_2$O) | (for C$_{23}$H$_{43}$N$_5$O$_{13}$.2H$_2$SO$_4$.7.5H$_2$O) Calcd (%): C,29.74; H,6.72; N, 7.54; S,6.90. Found (%): C,29.65; H,6.56; N, 7.52; S,6.88. | — |
| 1-N-(3-Hydroxypyrrolidine-3-carbonyl)kanamycin B sulfate | 64.5 | $[\alpha]_D^{23.0} = +71.8° \pm 1.1$ (c=1.004 in H$_2$O) | (for C$_{23}$H$_{44}$N$_6$O$_{12}$.2.5H$_2$SO$_4$.9.5H$_2$O) Calcd (%): C,27.27; H,6.76; N, 8.30; S,7.91. Found (%): C,27.11; H,6.41; N, 8.34; S,8.29. | — |

We claim:

1. A member selected from the group consisting of an aminoglycoside derivative of the formula:

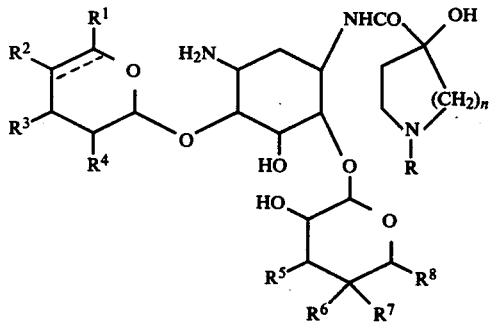

and a pharmaceutically acceptable salt thereof wherein R is hydrogen, alkyl of C$_1$ to C$_5$ or aralkyl of C$_7$ to C$_{10}$, R$^1$ is aminomethyl, hydroxymethyl, methylaminomethyl or 1-methylaminoethyl, R$^2$, R$^3$ and R$^6$ represent independently hydrogen or hydroxy, R$^4$ is hydroxy or amino, R$^5$ is amino or methylamino, R$^7$ is hydroxy or methyl, R$^8$ is hydrogen, hydroxymethyl or carbamoyloxymethyl, the dotted line represents the presence or absence of a double bond and n is an integer of 1 or 2.

2. A compound as claimed in claim 1, wherein R$^8$ is hydrogen or hydroxymethyl.

3. A compound as claimed in claim 1, wherein R$^1$ is aminomethyl or hydroxymethyl and R$^8$ is hydrogen or hydroxymethyl.

4. A compound as claimed in claim 1, wherein R$^1$ is aminomethyl or hydroxymethyl and R$^8$ is hydroxymethyl.

5. A compound as claimed in claim 1, wherein R$^1$ is aminomethyl, R$^2$ is hydroxy, R$^5$ is amino, R$^6$ is hydrogen, R$^7$ is hydroxy and R$^8$ is hydroxymethyl.

6. A compound as claimed in claim 1, wherein R is hydrogen.

7. A compound as claimed in claim 1, wherein R is C$_1$ to C$_5$ alkyl.

8. A compound as claimed in claim 1, wherein R is benzyl.

9. A compound as claimed in claim 1, namely 1-N-(4-hydroxypiperidine-4-carbonyl)kanamycin A.

10. A compound as claimed in claim 1, namely 1-N-(4-hydroxypiperidine-4-carbonyl)tobramycin.

11. A compound as claimed in claim 1, namely 1-N-(3-hydroxypyrrolidine-3-carbonyl)tobramycin.

12. A compound as claimed in claim 1, namely 1-N-(3-hydroxypyrrolidine-3-carbonyl)kanamycin A.

13. A compound as claimed in claim 1, namely 1-N-(3-hydroxypyrrolidine-3-carbonyl)kanamycin B.

14. A compound as claimed in claim 1, namely 1-N-(1-methyl-3-hydroxypyrrolidine-3-carbonyl)tobramycin.

15. A compound as claimed in claim 1, namely 1-N-(1-ethyl-3-hydroxypyrrolidine-3-carbonyl)tobramycin.

16. A compound as claimed in claim 1, namely 1-N-(1-isopropyl-3-hydroxypyrrolidine-3-carbonyl)tobramycin.

17. A compound as claimed in claim 1, namely 1-N-(1-benzyl-3-hydroxypyrrolidine-3-carbonyl)tobramycin.

18. A pharmaceutical composition which comprises a bactericidally effective amount of a compound or salt thereof as defined in claim 1 and a pharmaceutically acceptable carrier therefor.

19. A method for treating a gram-positive or gram-negative bacterial infection which comprises administering to a host suffering from said bacterial infection a bactericidally effective amount of a compound or salt thereof as defined in claim 1.

* * * * *